United States Patent [19]
Junker et al.

[11] Patent Number: 6,155,122
[45] Date of Patent: Dec. 5, 2000

[54] ADDITIVE FOR MOLTEN METAL SAMPLER

[75] Inventors: Thomas W Junker, Oconomowoc, Wis.; Richard A Falk, Hillsboro Beach, Fla.

[73] Assignee: Midwest Instruments Co., Inc., Hartland, Wis.

[21] Appl. No.: 09/056,496

[22] Filed: Apr. 7, 1998

[51] Int. Cl.[7] .................................................. G01N 1/12
[52] U.S. Cl. ..................................... 73/864.58; 73/864.56
[58] Field of Search ........................... 73/864.58, 864.55, 73/864.56, 864.57

[56] References Cited

U.S. PATENT DOCUMENTS

| | | | |
|---|---|---|---|
| 2,819,956 | 1/1958 | Strauss | 75/57 |
| 3,063,286 | 11/1962 | Nerheim . | |
| 3,295,171 | 1/1967 | Strange et al. | 73/864.58 X |
| 3,452,602 | 7/1969 | Hackett . | |
| 3,546,921 | 12/1970 | Bourker et al. . | |
| 3,646,816 | 3/1972 | Hance et al. | 73/DIG. 9 X |
| 3,686,949 | 8/1972 | Hackett | 73/DIG. 9 X |
| 3,783,694 | 1/1974 | Otte et al. . | |
| 3,805,621 | 4/1974 | Falk | 73/DIG. 9 X |
| 3,818,762 | 6/1974 | Kraus et al. . | |
| 3,844,172 | 10/1974 | Jeric | 73/DIG. 9 X |
| 3,946,594 | 3/1976 | Surinx | 73/DIG. 9 X |
| 4,002,072 | 1/1977 | Collins | 73/864.58 X |
| 4,010,649 | 3/1977 | Falk | 73/DIG. 9 X |
| 4,037,478 | 7/1977 | Cure | 73/DIG. 9 X |
| 4,059,996 | 11/1977 | Cure | 73/DIG. 9 X |
| 4,069,717 | 1/1978 | Falk . | |
| 4,107,393 | 8/1978 | Frantzreb, Sr. et al. | 428/558 |
| 4,121,749 | 10/1978 | Cure | 228/173 A |
| 4,140,019 | 2/1979 | Falk | 73/DIG. 9 X |
| 4,222,269 | 9/1980 | Falk . | |
| 4,261,740 | 4/1981 | Plessers | 73/864.58 X |
| 4,274,284 | 6/1981 | Hance . | |
| 4,570,496 | 2/1986 | Falk | 73/864.58 |
| 4,698,095 | 10/1987 | Ototani et al. | 75/58 |
| 5,014,561 | 5/1991 | Falk et al. | 73/864.53 |
| 5,057,149 | 10/1991 | Conti et al. | 75/377 |
| 5,187,991 | 2/1993 | Baerts | 73/864.56 |
| 5,305,658 | 4/1994 | Magee, Jr. | 73/864.82 |
| 5,393,497 | 2/1995 | Haber et al. | 738/864.82 X |
| 5,447,080 | 9/1995 | Falk | 73/864.58 |
| 5,524,497 | 6/1996 | Falk | 73/864.58 |
| 5,948,999 | 9/1999 | Falk et al. | 73/864.55 X |

*Primary Examiner*—Thomas P. Noland
*Attorney, Agent, or Firm*—Ryan, Kromholz & Manion, S.C.

[57] ABSTRACT

A sampling cavity for sampling molten metals includes a cavity body for receiving a measured sample of a molten metal, and, an insert containing a material for promoting carbide formation in the molten metal as it cools, the insert being in the form of an enclosed capsule formed of thin polymeric walls containing the material in finely divided solid form. The insert is embedded within a wall adjacent to a fill inlet passage.

11 Claims, 3 Drawing Sheets

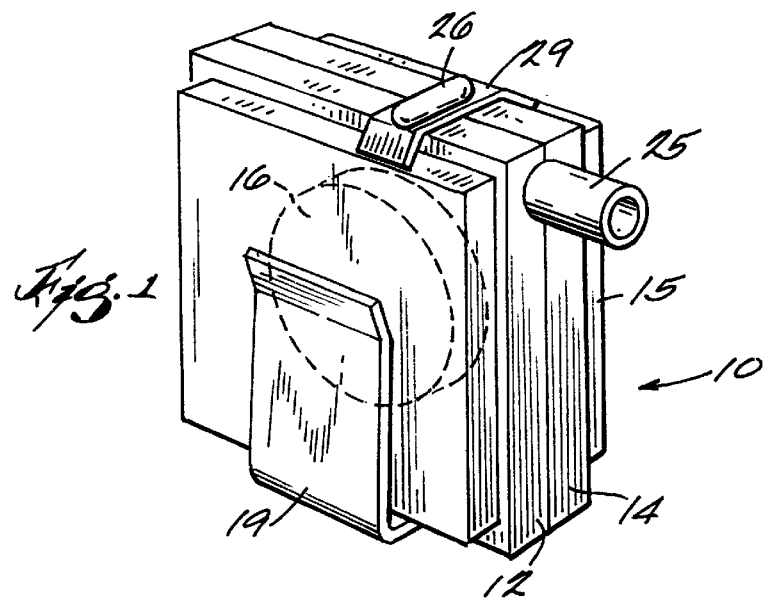
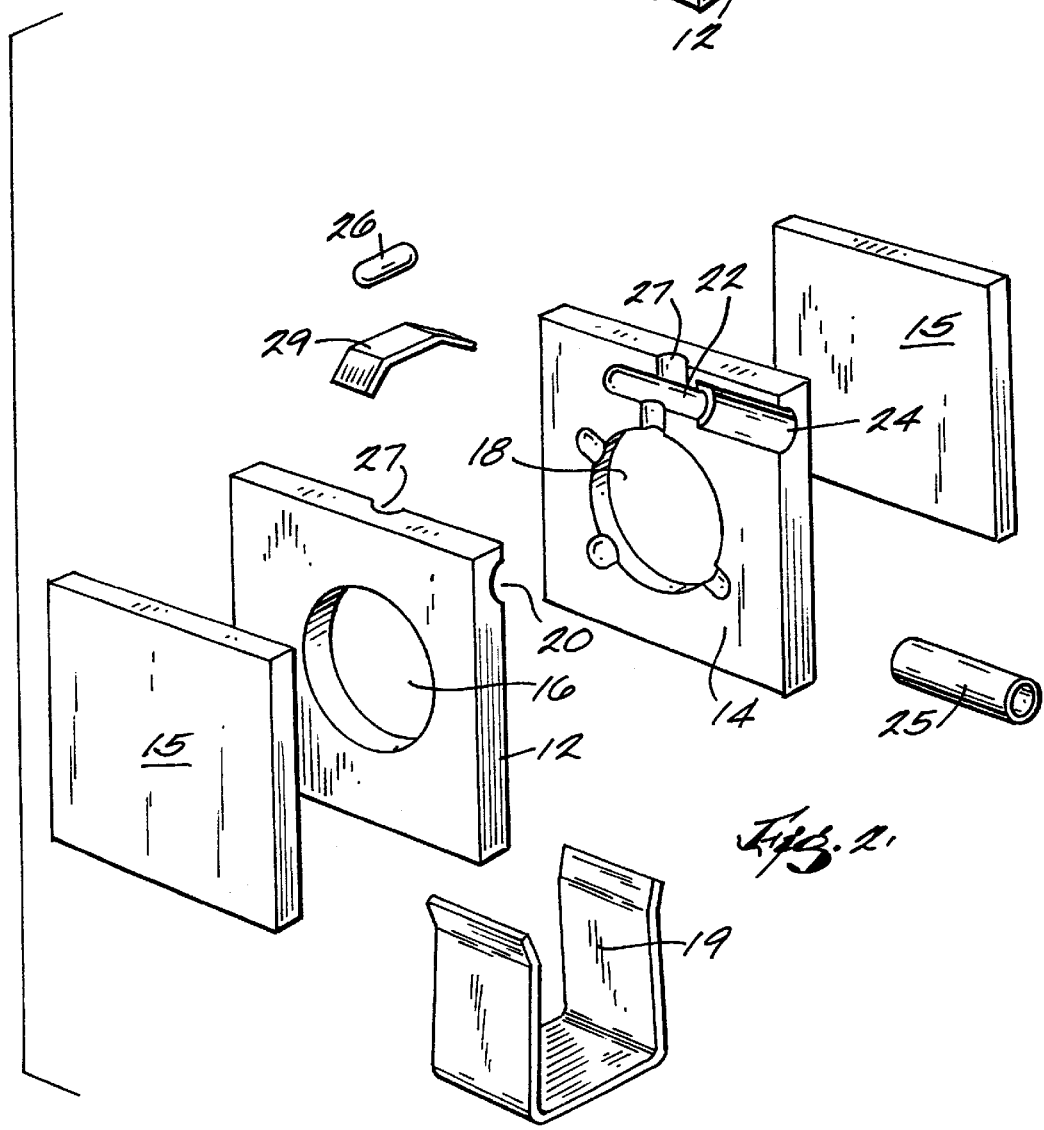

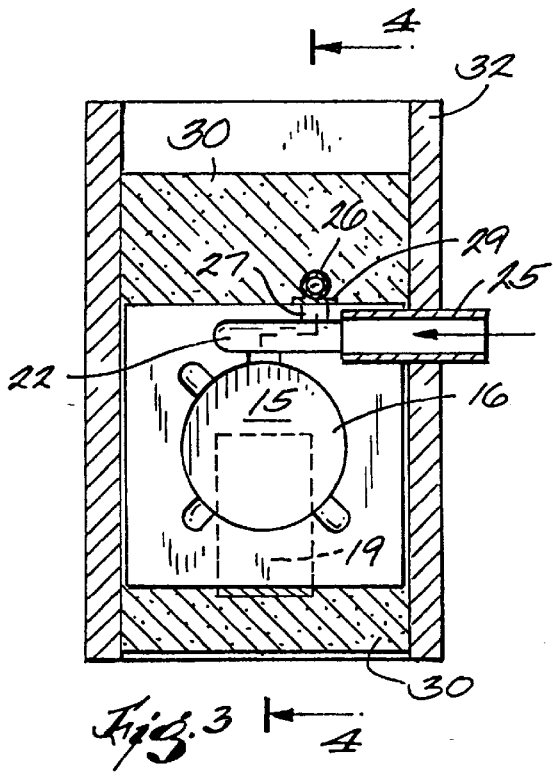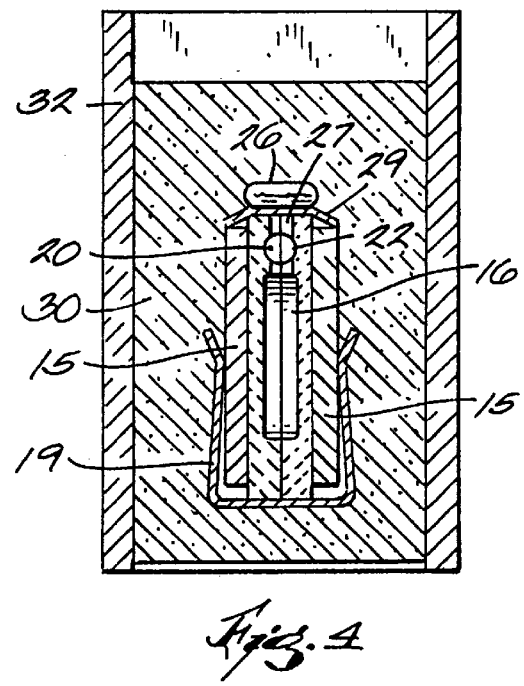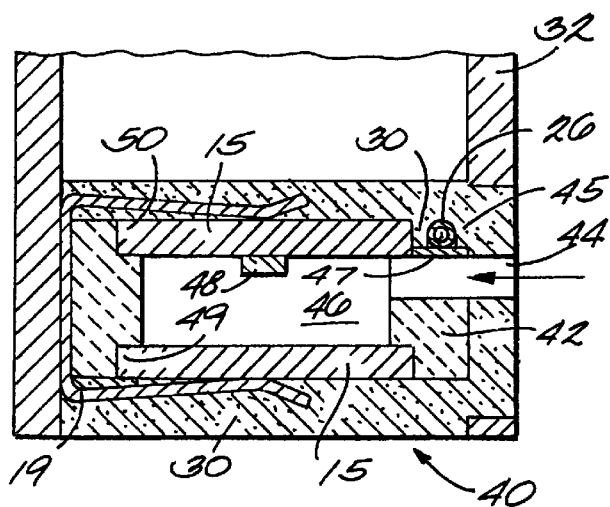

ADDITIVE FOR MOLTEN METAL SAMPLER

BACKGROUND OF THE INVENTION

The present invention relates to molten metal samplers. More specifically, the invention relates to devices having cavities for obtaining samples of a molten metal for the purpose of determining the composition or characteristics of the molten metal and wherein provision is made for adding a material for promoting carbide formation in the molten metal as it cools.

To spectrographically analyze a molten metal to determine its composition, it is common practice to obtain small sample castings or samples for analysis. In order to make an accurate analysis of molten iron, it is desirable to obtain samples of uniform composition, density and structure such as white iron, in which the carbon remains dissolved or interspersed in the metal in the form of a carbide instead of precipitating out in the form of graphite, which results in gray iron or spheroidal/nodular iron. Materials which deter graphite formation, such as tellurium, bismuth or antimony have been heretofore coated on mold surfaces fixed in the filling area, or have been placed in the mold in the form of an insert, for example, as described in Falk U.S. Pat. No. 4,570,496 issued Feb. 18, 1986. U.S. Pat. No. 4,059,996 shows a technique using a "blob" of such material in a cup type mold cavity. A device for providing an additive such as tellurium to a mold for obtaining samples for spectrographic analysis is described in U.S. Pat. No. 5,057,149 wherein the additive is placed between two flat metal layers. In U.S. Pat. No. 5,524,497 we described a device wherein the additive was contained in a combustible organic capsule. The present invention provides additional improved techniques for providing additives for consistently obtaining uniform, homogeneous dense, fine grained metallurgical white iron samples, even if the metal contains high carbon contents or has a high carbon equivalent. Carbon equivalent is defined in U.S. Pat. No. 3,546,921, issued Dec. 15, 1970.

SUMMARY OF THE INVENTION

An important aspect of the present invention is to provide an economical, low cost device for adding tellurium or a similar material to a cavity for obtaining samples of a molten metal for analysis in which carbide formation within the metal is promoted. A further aspect is to provide for such a device wherein an insert is used which provides for the addition of an accurately measured quantity of tellurium to a sampling cavity in a sample mold or cup, thereby assuring consistently accurate analyses, i.e., an accurately measured amount of tellurium is added to a measured volume of molten iron. Another advantage provided by the invention is the use of a low-temperature melting capsule fixed in a mold wall to provide rapid vaporization, dispersion and uniform mixing of the additive into the metal sample.

A still further aspect of the invention relates to protection of safety of workers by completely sealing the tellurium additive or similar hazardous material, and avoiding chipping, breaking or abrading off of such materials. A controlled amount of carbide formation promoting material is thus utilized for each use of a sampling cavity. A further aspect of the invention involves the baking of a sand-resin material to encase the capsule in a wall of the sampling cavity, where it is sufficiently exposed to molten metal entering the mold to rapidly vaporize and disperse therein. The capsule is located near the filling opening of a spectrographic sampling mold to effect desirable dispersion of the additive in the metal being sampled as it enters the mold cavity.

In a further embodiment the capsule is placed in a mold wall near the discharge end of a quartz fill tube, the position of which is fixed by means of a stop in the fill opening of the mold. Optionally, the insert can be located within a wall of the sampler, either in the sample cavity of the mold near the fill opening or within the wall of the fill opening, itself.

Briefly summarized, the present invention provides a device for sampling molten metals that includes a sample cavity for receiving a measured sample of a molten metal, and, an insert containing a material for promoting carbide formation in the molten metal as it cools, the insert being in the form of an enclosed capsule formed of thin-walled, light weight organic material embedded within a wall of the sampling device. The insert contains the carbide formation promoting material in finely divided solid form. The insert may be formed of any heat consumable material such as an organic polymer, paper, cellulose or the like. The material should be of a low, consistent low mass and have a low melting point or low flash point relative to the temperature of molten iron. The insert may be positioned adjacent to a fill inlet passage in the case of an immersion fill type sampling mold or in an interior wall of the sampler adjacent to the fill opening.

The cavity for immersion sampling molten metals may include a mold body formed of a single frangible mold body or may, alternatively, be formed of first and second mold halves. Each of the molds have peripheral edges and define a sample cavity having a fill inlet passage when the mold is assembled. The mold halves further define an opening for flow therein of molten metal during immersion of the mold into molten metal, which opening is connected to the sample cavity inlet so that molten metal can flow from the opening into the sample cavity. In one preferred embodiment, the mold has an opening adjacent to the opening which forms a flow path for molten metal to contact a capsule which is fixed in communication with the opening. The mold and capsule are embedded within a baked sand-resin body which houses the device. Details of such devices as further described in U.S. Pat. Nos. 4,069,717 and 4,140,019, which are incorporated by reference.

In accordance with the preferred embodiment, the carbide formation promoting material is tellurium. Other such materials can, however, be substituted.

BRIEF DESCRIPTION OF DRAWINGS

The invention will further be described in the following detailed description and accompanying drawings wherein:

FIG. 1 is a perspective view of the inner compartments of a mold and insert of this invention;

FIG. 2 is a perspective view of the components of FIG. 1 disassembled;

FIG. 3 is a central sectional view of a mold of FIG. 1 embedded in a sand-resin matrix;

FIG. 4 is a sectional view taken along line 4—4 of FIG. 3;

FIG. 5 is a central sectional view showing a further embodiment of the invention with parts broken away; and, FIG. 6 is a perspective view of the single piece mold body used in the embodiment of FIG. 5, also showing a tellurium-filled capsule in relation thereto.

DETAILED DESCRIPTION OF THE INVENTION

Figure 6:
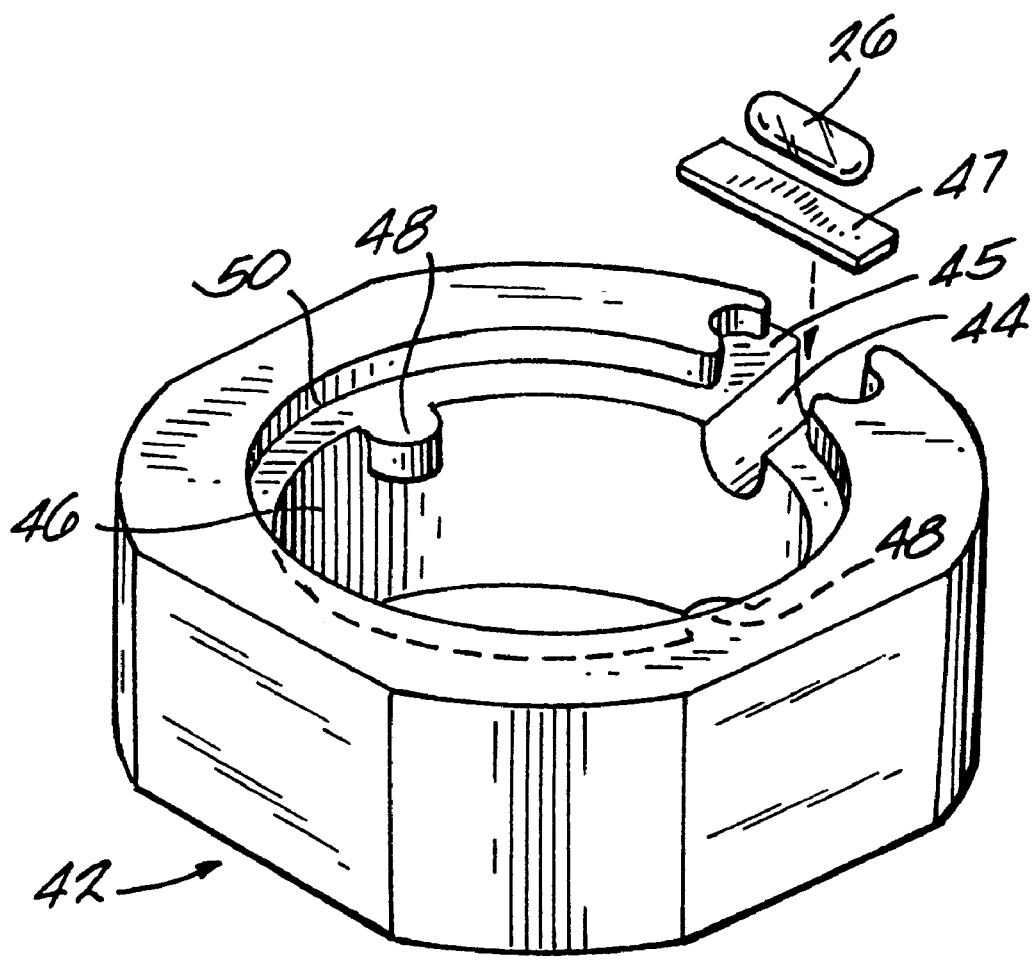

The inner component of a mold assembly 10 is seen in FIGS. 1 and 2 in assembled and separated condition, respectively. Mold 10 includes mold halves 12 and 14. The mold halves may be formed of any suitable heat-resistant material such as core sand, a ceramic or other refractory material. The sides are formed by mold-closing chill plates 15 of heat conductive metal such as steel in order to provide for rapid conduction of heat from the molten metal sample. A sample cavity is provided by aligned openings 16 and 18 in mold halves 12 and 14.

Any conventional clamping or attaching system such as a metal clamp 19 can be used for closing and holding the halves 12 and 14 of the mold together. Inlet passage 20, 22 is provided for introduction of molten metal into cavity 16. A widened opening portion 24, as shown, is provided for flow into the mold of molten metal to be sampled during immersion of the mold into molten metal and serves to receive and fix the position of a fill tube 25.

Insert 26 contains a material for promoting carbide formation in the molten metal as it cools. Preferably the insert is in the form of an enclosed capsule formed of thin walls formed of an organic material, such as a polymeric resin, containing the material, such as tellurium, in finely divided solid form. The material for promoting carbide formation, usually tellurium, is provided in a precise amount of high purity and of a preselected fine particle size and shape.

The insert 26 is positioned above an opening 27 which is connected to fill inlet passage 20, 22. Insert 26 is fixed in place by a baked sand-resin composition 30 subsequent to assembly of the mold halves 12 and 14, and is separated until use from passage 20, 22 by a thin sheet of paper or similar ablative material 29. The baked sand-resin mixture over the top of insert 26 permits breathing and escape of gases, such as combustion products of the capsule wall material, air contained in the mold, or excess carbide vapors, into the atmosphere.

Flow of molten metal through tube 25 into opening 20, 22 during immersion of the mold into molten metal causes controlled burning of sheet 29 and subsequent virtually instantaneous melting or vaporization of the walls of insert 26. Thus the tellurium in capsule 26 is released into the contents into the molten metal sample as it flows into the mold cavity 16, 18. The molten metal that flows through opening 20, 22 into cavity 16 thus becomes mixed with a sufficient amount of the tellurium in order to inhibit graphite formation during solidification and thus promote the formation of the desired white iron structure. The length of time needed to burn away the ablative sheet 29 to thus expose the tellurium containing capsule can be controlled by varying the thickness and composition of the sheet 29. After cooling of the metal, the mold halves 12, 14 (or frangible single piece mold in the case of mold 40 shown in FIGS. 5 and 6, described infra) are separated to yield a sample disc of metal for spectrographic analytical testing.

As seen in FIG. 3, the device 10 is enclosed in a layer of sand resin mixture 30 which is hardened by baking, usually at about 200–300° F. A container 32, often formed of cardboard or the like may be used to retain and shape the sand-resin mixture 30.

Another, commercially preferred, form of sampling mold 40 in connection with which the invention is used and which is commercially preferred is shown in FIG. 5. Mold 40 is particularly adapted for horizontally oriented immersion in a molten metal bath to withdraw a sample. Mold 40 is formed by a single piece frangible heat-resistant body 42, best seen in FIG. 6, having a fill opening 44.

Opening 44 has an interconnected adjacent opening 45 for receiving a capsule 26 transversely to fill opening 44. Sand-resin material 30 surrounds capsule 26 and fills the opening 45 thus shielding workers from exposure to the toxic contents of insert 26. A sheet of paper or plastic 47 can be used to temporarily separate capsule 26 from fill opening 44, and serves to support capsule 26 during the baking process. Similarly numbered parts of mold 40 are the same as those referred to with respect to mold 10. Horizontally oriented mold 40 produces a sample in mold cavity 46 which is desirably tested only in the region of its lower surface in the vicinity of lowermost chill plate 15. For this reason a marker 48, which may be sand-resin mixture, is embedded in the opposite surface for identification purposes. Recesses 49 and 50 are provided so that the chill plates 15 will be approximately flush with the outer surfaces of mold body 42.

Immersion of molds 10 or 40 in a molten metal bath to a depth at which the fill opening is totally submerged causes rapid melting of the outer skin of capsule 26 and allows the finely divided solid carbide-forming material within the capsule to vaporize and the resultant gases to be introduced into and flow with the molten metal into the mold cavity 16 or 46. Thus the carbide-forming material becomes uniformly mixed with the molten metal to promote carbide formation therein.

The capsule 26 may be formed of two telescoping halves in the nature of a pharmaceutical capsule or may be an entirely sealed capsule. The walls of the capsule can be formed of any thin, low mass combustible or vaporizable, non-contaminating material that disintegrates by melting and/or vaporization to release the contents of the capsule. Examples of suitable materials include gelatin, thermoplastic polymers, paper or similar substances. The particularly preferred materials in addition to gelatin are polymers such as a polyolefin, polyvinylchloride or polyvinylalcohol. The substitution of various other polymeric materials will be readily apparent to those skilled in the art. It is preferred that the walls of capsule 26 be formed of thermoplastic material so that the material instantaneously or rapidly melts upon contact with the molten metal. However, if desired, the capsule could, if desired, be formed of a thermosetting polymeric material. Insert 26 can also take the form of a small sealed plastic bag or wrap.

It will be apparent to those skilled in the art that numerous modifications of the afore described preferred embodiment can be made. For example, mold chill plate inserts 15 can be formed from various metals, for example, ductile iron, copper, or steel. With the addition of the carbide formation promoting material it is possible to utilize somewhat less heat conductive material for mold inserts than would otherwise be necessary. Previous methods of adding carbide formation promoting materials to mold often required contaminating binders or coating compositions which retard the release of the carbide former. In contrast, the present invention permits use of the materials in pure powder form and of precise particle size and shape which disperse more rapidly into the metal. It will also be appreciated by those skilled in the art that in addition to tellurium, various other carbide formation promoting materials can be substituted, for example, coating containing bismuth, antimony, boron, cesium or other similar materials known in the art or mixtures thereof.

In addition to the foregoing, various other modifications falling within the scope and spirit of the invention will be apparent to those skilled in the art.

What is claimed is:

1. A sampling device for sampling molten metals comprising:

said device including a mold having a sampling cavity for receiving a measured sample of a molten metal and a fill opening connected to said cavity, a passage in fluid flow communication with said fill opening, an insert containing a material for promoting carbide formation in the molten metal as it cools, said insert being in the form of a thin-walled enclosed capsule containing said material in finely divided solid form, the walls of said capsule being formed of a material that disintegrates when contacted by a molten metal, said insert being positioned in a recess in said sampling device in fluid flow contact with the interior of said mold, and, being embedded in a baked sand-resin composition which is formed over said insert.

2. A device according to claim 1 wherein said cavity is defined by mold halves of an immersion sampler, said mold halves having peripheral edges and openings in said mold halves to define a sample cavity having a fill inlet passage when said mold halves are assembled together, said capsule being positioned in a cavity adjacent to said fill inlet passage wherein it is embedded in said sand-resin body, an opening connecting said cavity to said fill inlet passage, said capsule being melted when molten metal flows into contact therewith to vaporize and release said material into said molten metal.

3. A device according to claim 1 wherein said carbide formation promoting material is selected from the group consisting of tellurium, bismuth, cesium, antimony, boron or mixtures thereof.

4. A device according to claim 1 comprising a one-piece heat-resistant body having a mold cavity closed on opposite sides by chill plates, said insert being embedded in said sand-resin composition which encloses said sampling device, said heat-resistant body, chill plates and capsule also all being embedded in said sand-resin composition.

5. A device according to claim 4 wherein said capsule is supported by sand-resin composition in a recess connected to said fill passage.

6. A device according to claim 1 wherein the capsule is positioned in a recess in contact with an opening connected to said fill passage and is embedded in-sand-resin material.

7. A device according to claim 1 wherein said capsule is formed of a material that melts when contacted by molten metal.

8. A device according to claim 1 wherein said capsule is formed of a material that vaporizes when contacted by molten metal.

9. A device according to claim 7 wherein the walls of said capsule comprise a thermoplastic organic polymer.

10. A device according to claim 1 wherein said capsule is separated from said fill opening by a sheet of ablative material which burns away when contacted by molten metal.

11. A device according to claim 1 wherein said sand-resin material over said capsule is sufficiently porous to permit venting of gases into the atmosphere.

* * * * *